(12) United States Patent
Zwolinski

(10) Patent No.: US 8,348,827 B2
(45) Date of Patent: Jan. 8, 2013

(54) SPECIMEN REMOVAL POUCH

(75) Inventor: Andrew M. Zwolinski, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 483 days.

(21) Appl. No.: 11/761,456

(22) Filed: Jun. 12, 2007

(65) Prior Publication Data

US 2008/0312496 A1 Dec. 18, 2008

(51) Int. Cl.
*A61B 1/00* (2006.01)

(52) U.S. Cl. ......... 600/104; 600/106; 600/153; 600/562

(58) Field of Classification Search ............... 600/104, 600/106, 153, 562
See application file for complete search history.

(56) References Cited

U.S. PATENT DOCUMENTS

| | | | |
|---|---|---|---|
| 5,037,379 A * | 8/1991 | Clayman et al. ............... 600/37 |
| 5,176,687 A * | 1/1993 | Hasson et al. ............... 606/114 |
| 5,370,647 A * | 12/1994 | Graber et al. ............... 606/127 |
| 5,480,404 A | 1/1996 | Kammerer et al. |
| 5,630,822 A * | 5/1997 | Hermann et al. ............. 606/114 |
| 5,681,324 A | 10/1997 | Kammerer et al. |
| 5,782,840 A * | 7/1998 | Nakao ............................ 606/114 |
| 5,810,806 A | 9/1998 | Ritchart et al. |
| 5,895,399 A * | 4/1999 | Barbut et al. ................. 606/159 |
| 6,036,698 A * | 3/2000 | Fawzi et al. ................... 606/114 |
| 6,306,081 B1 * | 10/2001 | Ishikawa et al. ............. 600/127 |
| 6,350,267 B1 | 2/2002 | Stefanchik |
| 6,383,197 B1 | 5/2002 | Conlon et al. |
| 6,406,440 B1 | 6/2002 | Stefanchik |
| 6,409,733 B1 | 6/2002 | Conlon et al. |
| 6,575,988 B2 | 6/2003 | Rousseau |
| 6,971,988 B2 | 12/2005 | Orban, III |
| 8,050,746 B2 * | 11/2011 | Saadat et al. ................. 600/476 |
| 2004/0242960 A1 * | 12/2004 | Orban, III ..................... 600/106 |

* cited by examiner

*Primary Examiner* — Max Hindenburg
*Assistant Examiner* — Renee Danega
(74) *Attorney, Agent, or Firm* — Porter Wright Morris & Arthur LLP

(57) ABSTRACT

A method and apparatus for use during a surgical procedure sealingly isolates a resected specimen to prevent contamination of surrounding tissue as the specimen is removed from the surgical site. The pouch is disposed at the distal end of an endoscope or trocar, and can be used to debulk and dimensionally alter the specimen for removal through a working channel.

12 Claims, 9 Drawing Sheets

SPECIMEN REMOVAL POUCH

FIELD OF THE INVENTION

The invention relates generally to pouches for removing specimens during surgical procedures and more particularly to a flexible pouch for use with a structural pathway, such as a trocar or endoscope, in isolating and removing surgical specimens during a laparoscopic or endoscopic procedure.

BACKGROUND

Under current surgical procedures, tissue that is to be removed from the body during laparoscopic or endoscopic procedures typically is resected and thereafter simply engaged by a grasping element and pulled out of the body. In many instances, the removed tissue is infected or may contain cancerous cells. Under these circumstances it is highly desirable to avoid contact between the tissue being removed and other healthy tissue situated along the exit path for the removed tissue. The need for avoiding contact between the tissue being removed and the tissue situated along the exit path is particularly pronounced when, as is frequently the situation, the tissue situated along the exit path has been traumatized from insertion of the endoscope or trocar. Unfortunately, particularly when the surgical procedure is conducted in a closely confined space, such as during laparoscopic or endoscopic procedures, inadvertent contact between the infected or cancerous tissue being removed and healthy tissue situated along the exit path sometimes occurs. As a consequence, infected or metastatic cells from the resected tissue being removed may come into contact with healthy tissue and spread the infection or deposit metastatic cells on the healthy tissue.

Specimen retrieval bags are sometimes used for the removal of resected tissue or organs in endoscopic procedures. For example the Endopouch Retriever sold by Ethicon Endo-Surgery, Inc. includes two retractable support arms that are secured to the opening of a net-like specimen bag formed of polypropylene. By remotely retracting the support arms, the bag can be closed in a clinched position to secure specimens in the bag for removal from the body. These prior art specimen bags, however, are unsuitable for removal through an access channel of an endoscope or trocar and do not isolate the resected tissue from healthy tissue situated along the exit path. In addition, due to its large size, the resected tissue frequently is dimensionally incompatible with the relatively small size of and access channel extending through an endoscope or trocar. Consequently, the bag must be removed through an auxiliary opening into the body cavity formed by a separate incision, or the endoscope or trocar must be removed prior to the removal of the tissue.

Another endoscopic tissue retrieval apparatus is disclosed in U.S. Pat. No. 6,971,988 to Orban, III. In this latter-mentioned device, a pair of expandable hoop-like support members, spaced by a plurality of stuts support a flexible pouch. The device is slideably translatable within a lumen of an endoscope. When moved out of the distal end of the lumen, the hoop-like member automatically expands to open an end of the pouch. A pair of drawstrings are provided to close the hoop-like support members whenever a specimen is placed in the pouch. Among other disadvantages, the Orban device utilizes one of the tool channels of the endoscope, reducing the flexibility of the endoscope's usage. In addition, this pouch mechanism lacks the ability to dimensionally alter the specimen.

BRIEF SUMMARY

One example of the invention is a method of removing a specimen resected during a surgical procedure. The method includes the steps of securing a first end of a barrier pouch having first and second ends and continuous barrier surface that defines an interior lumen extending between the first and second ends. The first end of the barrier pouch is secured to a structure located proximal to an end opening of a pathway structure having an internal passageway. The connection between the barrier pouch and the structure permits fluid communication between the interior lumen of the pouch and the internal passageway of the pathway structure. With the second end of the barrier pouch in an open position, a surgically resected specimen is positioned in the barrier pouch and the specimen is positioned within the interior lumen of the barrier pouch while the pouch is located at a surgical site. The second end of the pouch is then sealingly closed to encapsulate the specimen in the pouch to isolate the specimen from the environment external to the barrier pouch. The specimen is then removed from the surgical site.

According to another example of the invention, work is performed on the specimen to reduce a least one of its dimensions after the specimen is isolated from the environment external to the barrier pouch. This work may be performed prior to removing the specimen from the surgical site.

According to another example of the invention, work on the specimen by applying a vacuum to the interior lumen of the barrier pouch and compressing the specimen with an internal portion of the barrier pouch surface.

According to get another example of the invention, the work performed on the specimen includes at least partially liquefying the specimen, and further includes the step of removing the liquefied portion of the specimen from the barrier pouch under the influence of the vacuum applied to the interior lumen of the barrier pouch. This liquid removal may be performed while the barrier pouch remains at the surgical site.

According to another example of the invention, the work performed on the specimen includes mechanically penetrating the specimen with a cutting instrument.

Another example of the invention provides a removable retainer for selectively and releasably securing the first end of the pouch about the external surface of the structural pathway.

In yet another example of the invention, a pouch is provided for capturing tissue resected during a surgical procedure. A flexible barrier pouch having first and second ends with a continuous barrier surface extends between the first and second ends. The barrier pouch is configured to define an internal lumen extending between the first and second ends. The first end of the barrier pouch is adapted for connection to a first structure for holding the first end of the barrier pouch in an open position that permits communication between the internal lumen of the barrier pouch and an interior passage of a pathway structure. The second end of the barrier pouch is connected to the movable support structure with the movable structure being operative to move the second end of the barrier pouch longitudinally between a first retracted position and a second deployed position. The movable structure is also operative to move the second end of the barrier pouch from a first open position creating an ambient environment opening to the internal lumen of the barrier pouch to a second closed position in which the internal lumen of the barer pouch is sealed from the ambient environment.

In a further example of the example, the internal lumen of the barrier pouch is in fluid communication with a vacuum source.

BRIEF DESCRIPTION OF THE DRAWINGS

While the specification concludes with claims which particularly point out and distinctly claim the invention, it is believed the present invention will be better understood from the following description taken in conjunction with the accompanying drawings, in which like reference numbers identify the same elements in which:

Reference will now be made in detail to certain exemplary embodiments of the invention, examples of which are illustrated in the accompanying drawings.

DETAILED DESCRIPTION OF EXEMPLARY EMBODIMENTS

Figure 1:
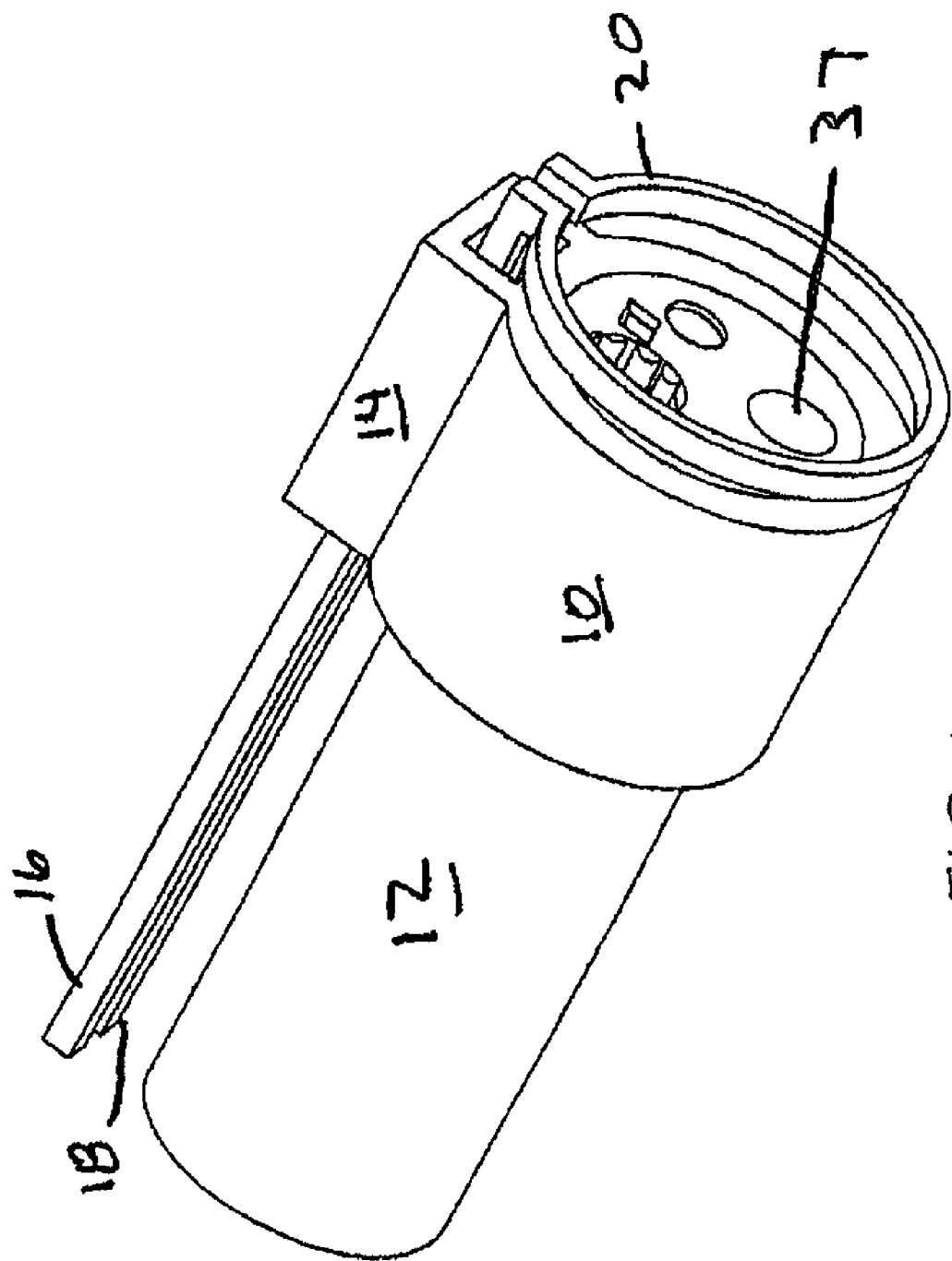
FIG. 1 is a schematic perspective view of a structural pathway, such as an endoscope or trocar, with a non-deployed pouch mechanism constructed in accordance with the principles of the present invention disposed on the outer surface of the distal end of the pathway structure.

Referring now to the drawings, FIG. 1 shows a simplified form of one exemplary embodiment of the invention in which a first outer support member 10 is secured to the outer circumferential surface of the distal end of a pathway structure 12, such as an endoscope or trocar. The outer support member 10, which is stationary relative to the pathway structure 12 in the exemplary illustrated embodiment, includes a channel guide 14 adjacent to the outer surface of the pathway structure 12. The channel guide 14 supports, and confines the movement of a pair of flexible cord-like actuator components 16 and 18 that terminate on their distal ends in a flexible movable noose-like support structure 20, which support structure 20 has a generally circular configuration in the specifically illustrated embodiment. As explained in greater detail below in connection with the description of FIG. 10, the actuator components 16 and 18 may be slidably contained with a sheath 19 (see FIG. 10), which sheath 19 is omitted from FIGS. 1-9 for clarity of illustration. In one exemplary embodiment of the invention, the flexible cord like actuator components 16 and 18, as well as the noose-like support structure 20 may be formed of any number of suitable materials. One exemplary material is a shape memory material such as one of the family of inter-metallic metals formed from a nearly equal amount of nickel and titanium, partially available under the designation Nitinol (an acronym for Nickel Titanium Naval Ordinance Laboratory). Another exemplary material for the actuator components 16 and 18 is a stainless steel braid. The specific form of support structure 20 and actuator components 16 and 18 illustrated in the drawings is in the form of a snare. It will be readily appreciated, however, that various other forms of support structures and actuator components may be used according to the principles of the invention.

Figure 2:
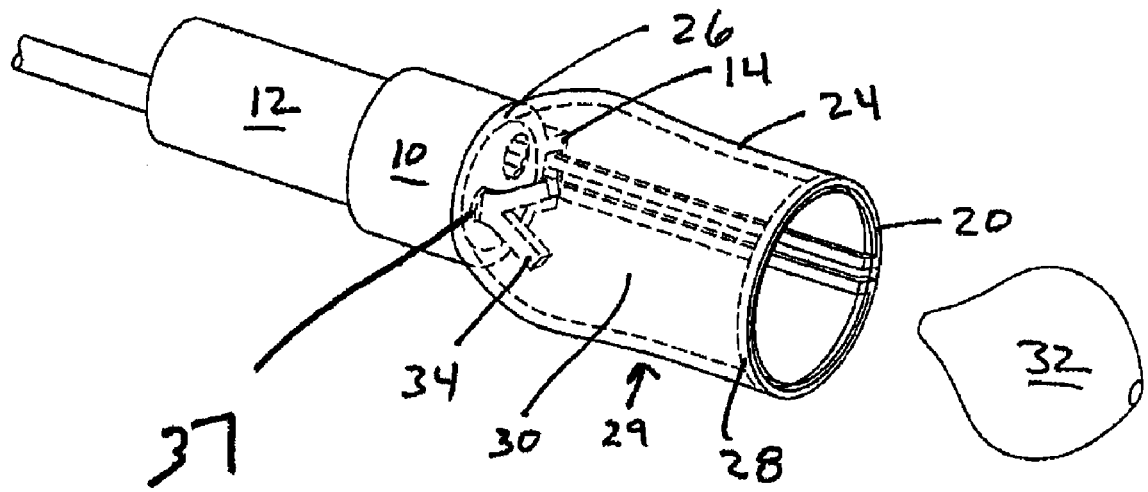
FIG. 2 is a schematic perspective view of the structural pathway and pouch mechanism depicted in FIG. 1 with the pouch mechanism longitudinally moved relative to the depiction of FIG. 1 to a deployed position and the distal end of the pouch open to the ambient environment at a surgical site.

As will be apparent from a comparison from the illustrations of FIG. 1 and FIG. 2, the support number 20 is longitudinally movable from a first retracted position, shown in FIG. 1, to a second the deployed position illustrated in FIG. 2. The support number 20 supports a continuous flexible barrier membrane 24 that extends from a first proximal end 26 to a second distal end 28 to form a pouch 29. The second end 28 of the barrier material 24 may be attached to the pathway structure 12, either directly, or as in the exemplary embodiment, indirectly through the support structure 20. Such attachment may be achieved in a variety of ways, as for example, as shown in the exemplary embodiment illustrated, by folding the barrier material 24 back on itself to form an internal channel. The support number 20 could then extend through this internal channel erected in the distal end of the barrier membrane 24 so that the support member 20 is completely encased by the barrier material 24. Alternatively, the barrier material 24 can be attached to the support member 20 by an adhesive, or by a RF welding. Other alternatives of securing the barrier material to the support number 20 include an interference fit or overmolding the clamp to the barrier material 24. The barrier membrane 24, from a variety of materials, as for example, may be formed of polyethylene or another type of polypropylene material. Irrespective of the material, the barrier material forms a continuous barrier surface between the first and second ends 26 and 28 respectively and defines an internal lumen 30 extending therebetween. The first end of the pouch 29 is sealingly secured in the specifically illustrated embodiment to the outer support number 10 so that the first end of the pouch 29 is open to the distal end of the pathway structure 12, permitting fluid communication between the pouch lumen 30 and a working channel 37 extending through the pathway structure 12. Since the outer support number 10 is itself sealingly interconnected with the pathway structure 12, sealingly securing the pouch 29 to the support member 10 effectively forms a sealed relationship between the pouch 29 and the pathway structure 12. It will be readily appreciated, however, that other types of sealing relationships between the pouch 29 and the pathway structure 12 may be utilized, such as directly sealing the pouch 29 to the pathway structure 12, rather than indirectly sealing the two components, as specifically illustrated in the drawings.

Figure 3:
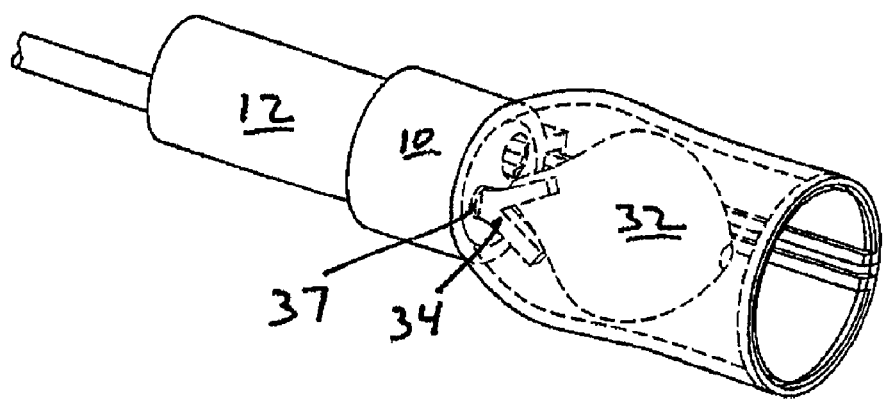
FIG. 3 is a schematic perspective view similar to FIG. 2 showing a tissue specimen after the specimen has been removed and placed within the pouch.

FIG. 2 also schematically illustrates a surgically resected tissue specimen 32 positioned in proximity to the second end of the barrier pouch 29. As shown in FIG. 3, this specimen 32 may be engaged by a grasping element 34 and pulled into the interior lumen 30 of the pouch 29. It will be appreciated by those skilled in the art that the grasping element 34 (the end effector of which is illustrated in each of FIGS. 2-4) extends through a working channel 37 of the pathway structure from a location external to the patient. The grasping element 34 is selectively moved longitudinally by an actuator (not shown) located at the proximal end of the pathway structure 12, which actuator element may be in the form of a handle for manually moving the grasping element 34, as is well known in the art. Regardless as to whether the grasping element 34 is moved manually or by a more sophisticated actuator, the illustrated end effector 34 is moved through the interior of lumen 30 of the barrier membrane 24 and through the opening at the distal end of the barrier membrane 24 formed by support number 22 as the end effector 34 is longitudinally advanced. When the grasping element 34 is longitudinally extended sufficiently to position its end effector adjacent to the specimen 32 (typically with the end effector extending out of the internal lumen 30, not shown), the end effector of the grasping element 34 engages the specimen 32 and pulls that specimen 32 into the interior lumen 30 as the grasping element 34 is retracted. FIG. 3 shows the specimen disposed within the interior lumen 30 of the pouch 29 after it has been engaged by the grasping element 34 and pulled into the interior lumen 30.

Figure 4:
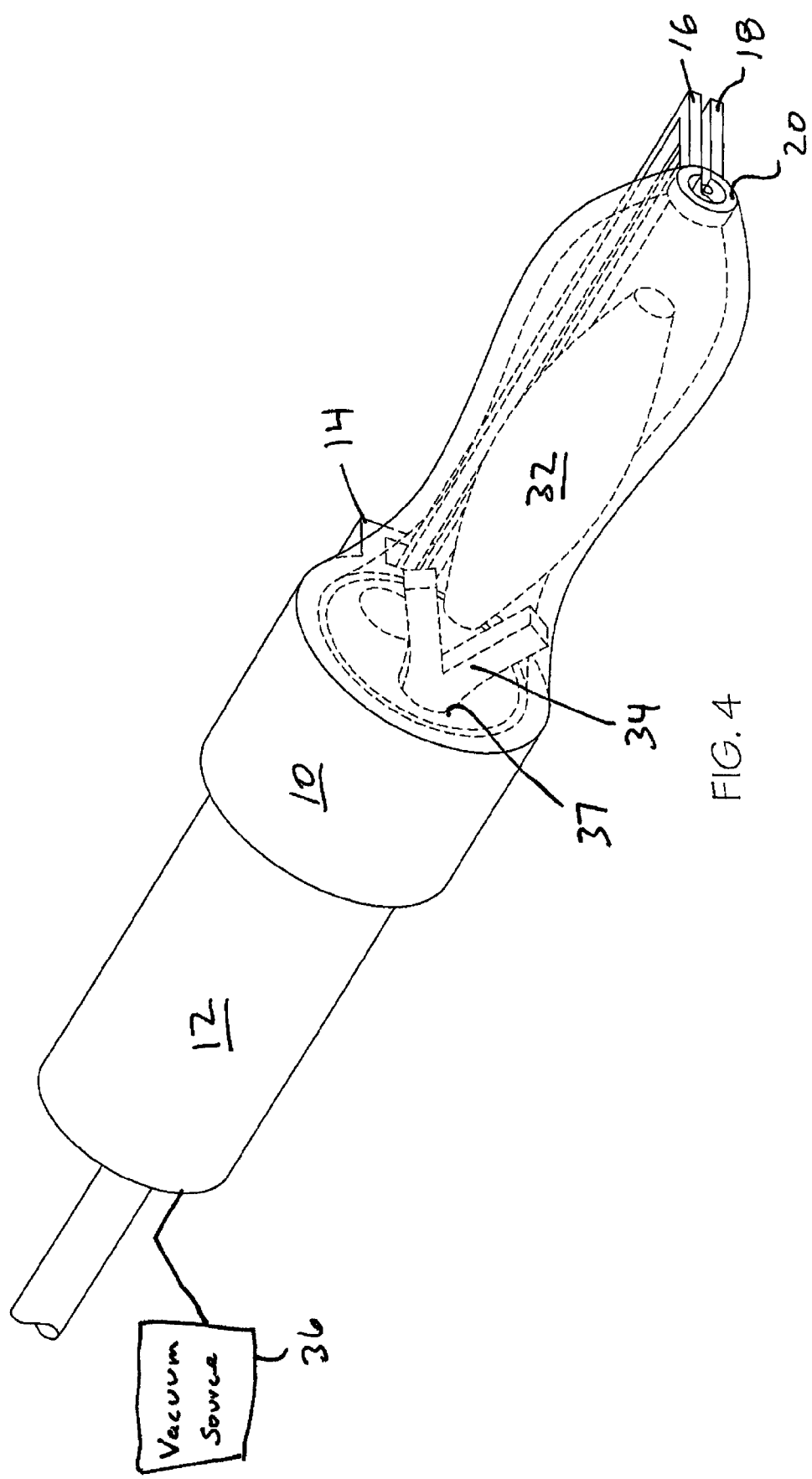
FIG. 4 is a schematic perspective view of the pouch mechanism of FIG. 3 showing the open end of the pouch in a sealed clinched position with the specimen sealed within the pouch after the specimen has been reduced in volume.

After the specimen 32 is captured inside the interior lumen 30, the support structure 20 is reduced by retracting (from a location external to the patient) one or both of the cord-like actuator components 16 or 18. As the opening defined by the support structure 20 is reduced in size by a retraction of the actuator components 16 or 18, the second or distal end of the pouch 29 is closed. Compressive force provided by the noose-like support structure 20 against the barrier material surrounding the support structure 20 seals the distal end of the pouch 29 and isolates the specimen 32 from the environment external to the pouch 29. FIG. 4 shows the second or distal end 28 of the pouch 29 as it is clenched by the support member 20 to seal the second or distal end 28 of the pouch 29. As noted above, the membrane forming pouch 29 is continuous and impervious to the resected specimen and constituents or substances that might emanate from the specimen. Consequently, with the first end 26 of the pouch 29 sealed relative to the pathway structure 12, and the second end 28 sealed by the support number 20, the specimen 32 is isolated from the environment external to the pouch 29. It will be appreciated that isolating the specimen 32 in this manner allows removal of the specimen 32 from the surgical site with minimal risk of contamination of tissue adjacent to the exit passage.

FIG. 4 shows the specimen 32 contained within the interior lumen 30 of the pouch 29 isolated from the environment external to the pouch 29. Due to their large size, resected tissue specimens, such as the specimen 32 illustrated in the drawings, are frequently dimensionally incompatible with the access channels which expand through surgical instruments, such as endoscopes or trocars. For this reason, it also may be desirable to reduce at least one dimension of the specimen 32 to permit its removal from the surgical site through an access channel 37 of the structural pathway 12. One method by which the dimensions of the resected specimen 32 might be reduced is by compression. As suggested by the depiction of FIG. 4, this can be accomplished by applying a vacuum to the interior lumen 30 of the pouch 29 (through the working channel 37). As schematically illustrated in FIG. 4, the interior lumen 30 of pouch 29 is in fluid communication with a vacuum source 36. The vacuum source 36 may be either a vacuum port typically provided in a surgical suite or an independent dedicated vacuum source. In either event, application of a vacuum to the interior lumen 30 of the pouch 29 causes the barrier material 24 to collapse, applying a compressive force upon the specimen 32. Since the specimen 32 frequently is composed of a high percentage of water, substantial compression of the specimen 32 not only dimensionally changes the specimen, it debulks the specimen 32 by breaking it and releasing water contained within the cells of the specimen 32. Any released liquid is then withdrawn by the influence of the vacuum through the working channel 37 of the structural pathway 12 and collected at a site external to be patient. With sufficient compression and sufficient withdrawal of the released liquid, is been found that the specimen 32 may be dimensionally reduced to a size sufficient to permit removal of the specimen 32 through the working channel of the structural pathway 12.

It will be appreciated that the specimen 32 also may be dimensionally altered or debulked by methods other than that vacuum induced compression. Once the distal end of the pouch 29 is sealed and the specimen 32 is isolated in the interior of lumen 30 of the pouch 29 from the surgical slight, the specimen could be dimensionally reduced in a number of different ways. For example, the specimen 32 could be mechanically altered by a needle knife advanced into the interior lumen 30 through another working channel of the structural pathway 12, such as the working channel 37 illustrated in FIG. 4. The needle knife (not illustrated) could be used to mechanically alter or cut or the contained and isolated specimen 32. Such mechanical alterations or mutilation of the specimen 32 will similarly release liquid from the specimen 32, which liquid can be removed from the interior lumen 30 by the influence of the vacuum source 36. Again, with sufficient mechanical alterations in removal of released liquid, the specimen 32 may be dimensionally reduced to permit its removal through the working channel 37, as shown in FIG. 4.

It also may be desirable, once the specimen 32 is captured in the pouch 29, to access the area from which the specimen was taken, as for example, to repair that tissue area or to close any defects made during the resection process. In order to facilitate access to this area of the tissue, it may be desirable to free the proximal end of the pouch 29 from the structural pathway 12. By removing the proximal portion of the pouch 29 from the distal portion of the pathway structure 12, the resection area can be accessed with tools passing through the working channel 37 of the pathway structure 12. One exemplary mechanism for accomplishing this objective is shown in FIGS. 5-9.

Figure 5:
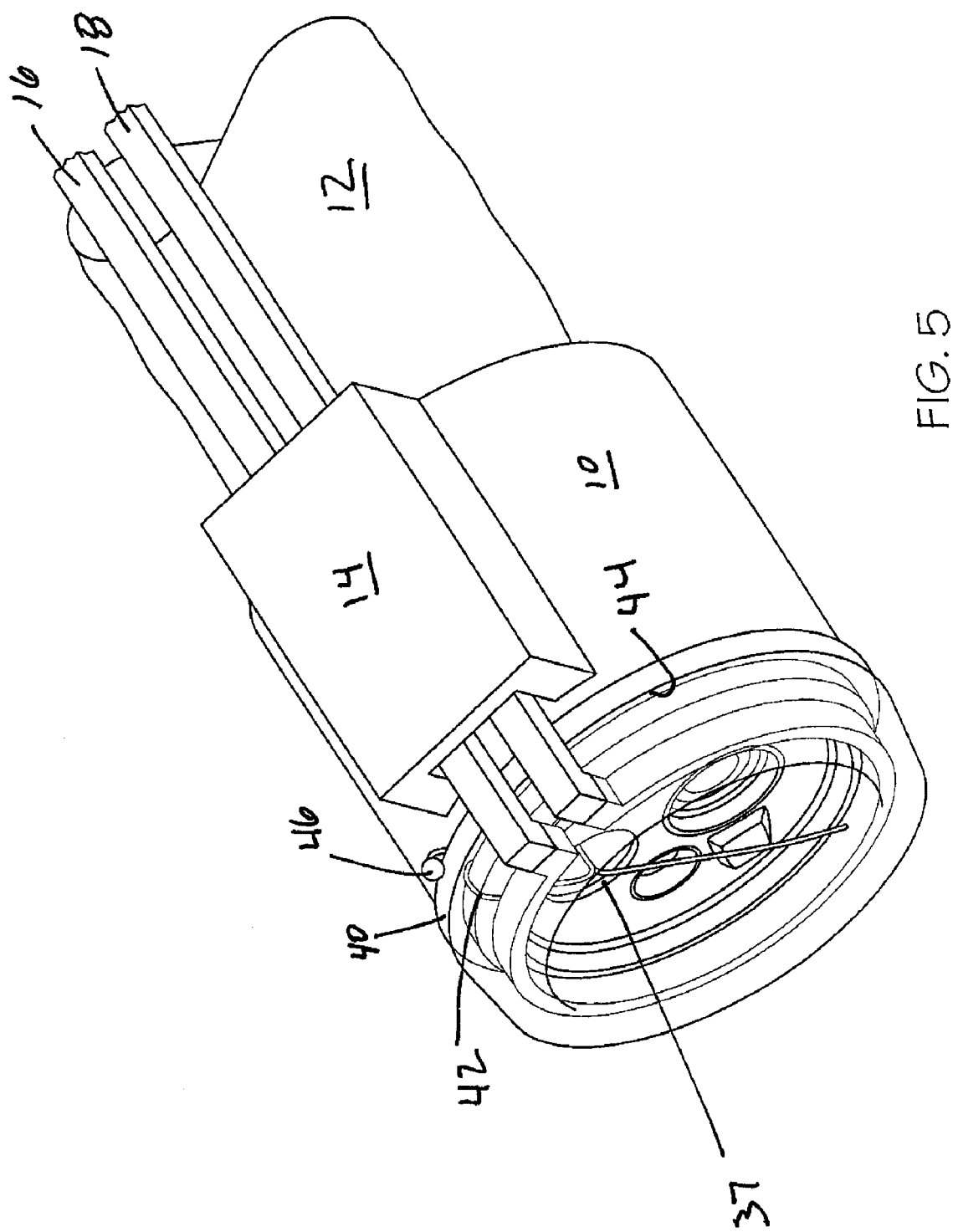
FIG. 5 is a schematic perspective view of a pathway structure similar to the view of FIG. 1, but further showing an elastomeric member releasably securing the pouch mechanism to the pathway structure and an actuation wire for effectuating release of the pouch mechanism from the pathway structure.

Referring specifically to FIG. 5, the distal end of the pathway structure, again specifically illustrated as a endoscope 12 in the exemplary embodiment, is shown with an outer support member 10 disposed about its outer distal surface. As in the previously described embodiment, the outer support member 10 includes a channel guide 14 for actuator components 16 and 18, both of which are disposed in an outer sheath 19 (see FIG. 10). In the specific exemplary embodiment illustrated in FIG. 5, however, the proximal end of the pouch 29 is removably secured to the structural pathway 12 by a selectively releasable retainer, specifically illustrated as an elastomeric member 40. The elastomeric member 40, essentially having a "rubber band" type configuration, may be disposed within a circular channel or pocket formed in the proximal end of the pouch 29. This circular channel or pocket may be formed in a manner similar to circular channel formed in the distal end 28 of the pouch 29, as for example, by folding the pouch material back on itself. In the retracted state shown in FIG. 5, the elastomeric member 40 is positioned within a correspondingly shaped circular groove 44 (see FIG. 9 also) in the cap on the end of the structural pathway 12. The elastomeric member 40 applies a compressive force against the proximal end of pouch 29, thereby providing a sealing relationship between the pouch 29 and the outer cap 10 and thereby releasably securing the pouch relative to the structural pathway 12.

Figure 6:
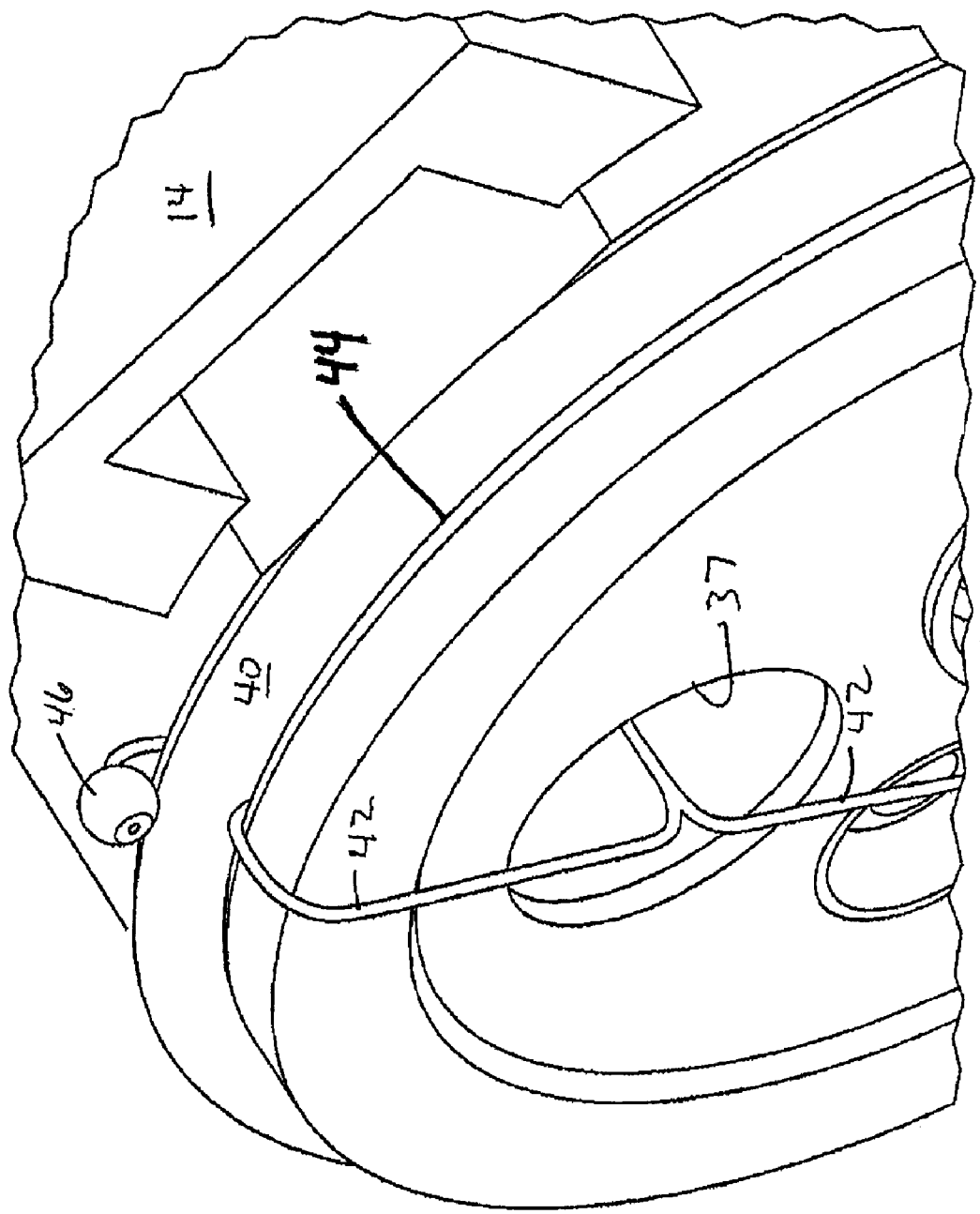
FIG. 6 is a enlarged perspective view of a portion of the pathway structure and pouch mechanism of FIG. 5 depicting a bead on the end of an actuation wire.
Figure 7:
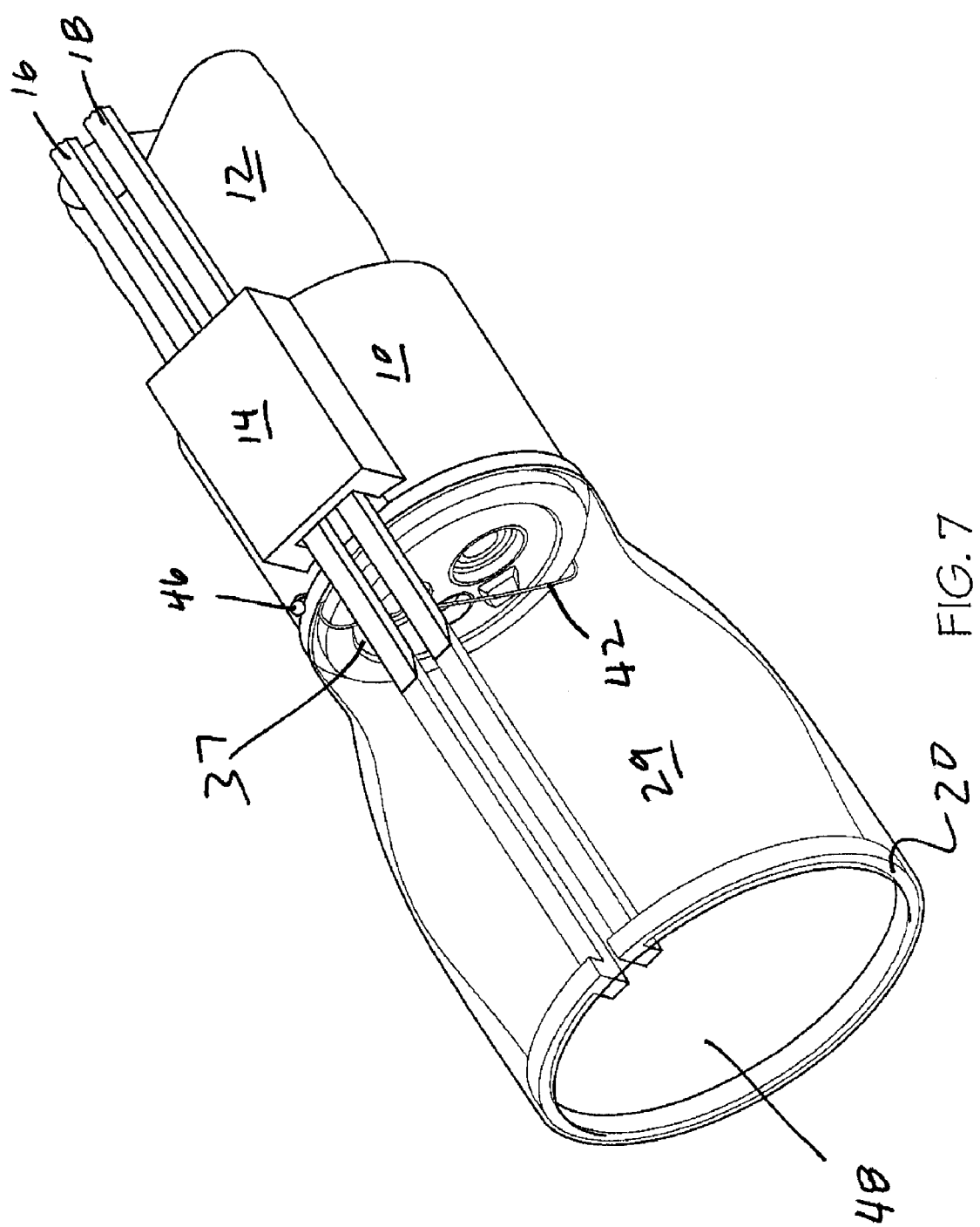
FIG. 7 is schematic perspective view of the pathway structure and pouch mechanism of FIG. 5, but showing the pouch mechanism in a deployed position with the distal end of the pouch in a fully open position.

As more clearly shown in FIG. 6 (which omits the actuator members 16 and 18, and the sheath 19, for clarity of illustration), two actuation flexible cordlike members 42 extend outwardly in opposite radial directions from a working channel 37. Any number of actuator members 40 can be utilized, such as strings, braided suture, wires or ropes, etc. Each of these actuation members 42 extends around the proximal end of the pouch 29 (on opposite sides of the structural pathway) to a position outside of the pouch 29, passing in the space between the pouch 29 and the groove 44 (partially obscured by elastomeric member 40) on the outer cap 10. A bead 46 (only one of which is shown in FIGS. 5 and 6) is positioned on the outward portion of each of the actuation members 42 on the outside side of the elastomeric member 40. When tension is applied to the actuation members 42, as for example from pulling the wires from a location outside the patient, the beads 46 are pulled against the elastomeric member 40, causing the elastomeric member 40 to dislodge from the groove 44 in the outer cap 10.

FIGS. 5-9 show a typical operational sequence for this second illustrated exemplary embodiment. An endoscope, the specific type of structural pathway illustrated in these exemplary drawings, is typically introduced into a body cavity with the pouch mechanism is a retracted position, as shown in FIGS. 5 and 6. Once positioned at the resection site, that is, in proximity to the tissue to be resected, the pouch mechanism 29 is moved to the deployed position illustrated in FIG. 7, a position in which the pouch 29 is translated longitudinally relative to the depiction of FIG. 5. In the position shown in the illustration of FIG. 7, the support member 20 is enlarged to form an aperture 48 at the distal end of the pouch 29, and the pouch 29 is prepared for the introduction of a specimen.

Figure 8:
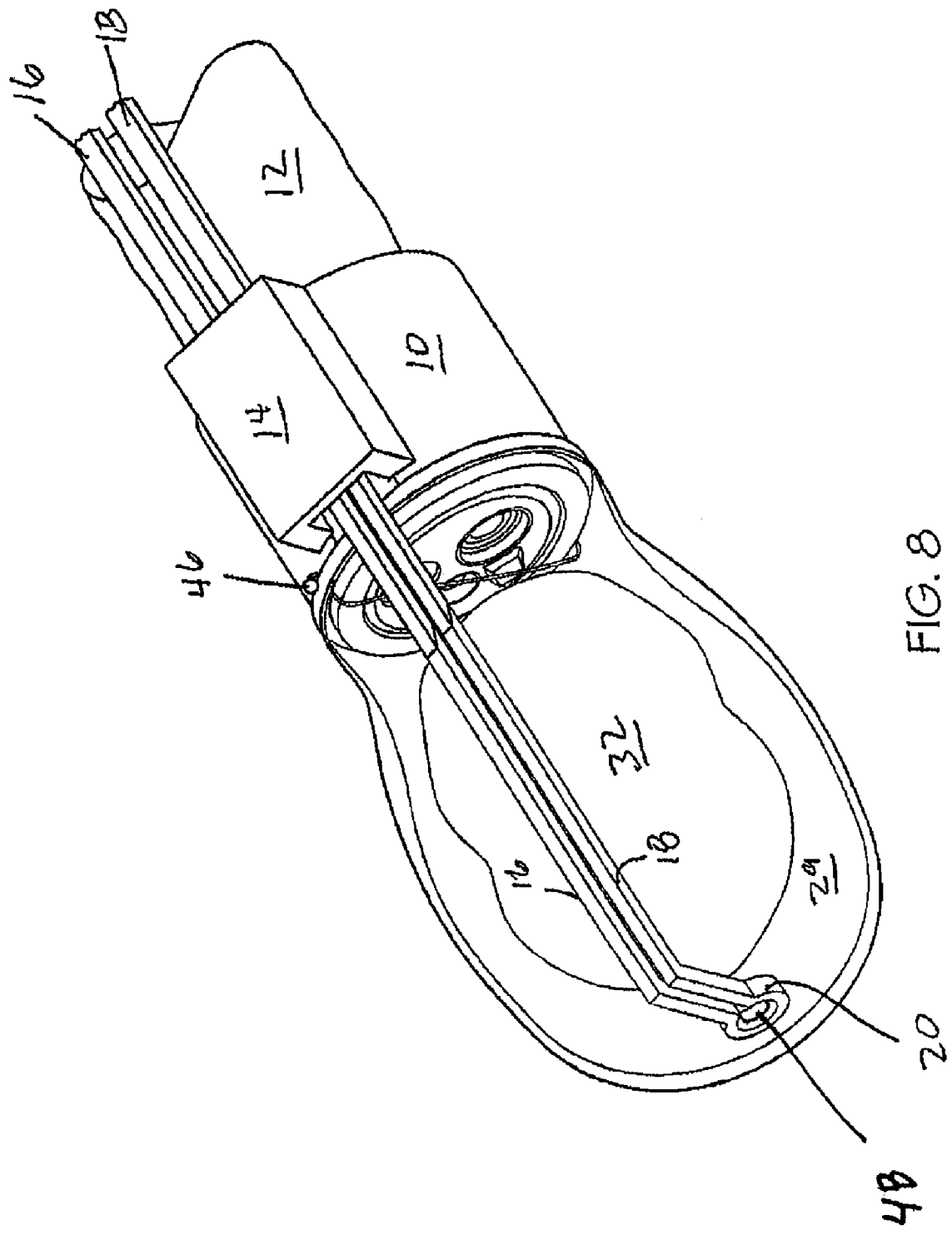
FIG. 8 is a schematic perspective view of the pathway structure and pouch mechanism of FIG. 6 after a specimen has been disposed in the pouch and the distal end of the pouch has been closed.

FIG. 8 shows the pouch assembly following introduction of a specimen 32. In this illustration, the aperture 48 at the distal end of the pouch has been closed and sealed by retracting (from a location external to the patient) one or both of the cord-like actuator components 16 or 18. As explained in connection with the previously described exemplary embodiment, retraction of the actuator components 16 and/or 18 closes and seals the opening 48 defined by the support structure 20. After capturing and isolating the specimen 29 in the pouch 29, work can optionally be performed on the specimen, as for example by withdrawing air through one of the working channels in the structural pathway and applying a vacuum to the interior of the pouch, or by mechanically altering the specimen 32 with a penetrating instrument.

Figure 9:
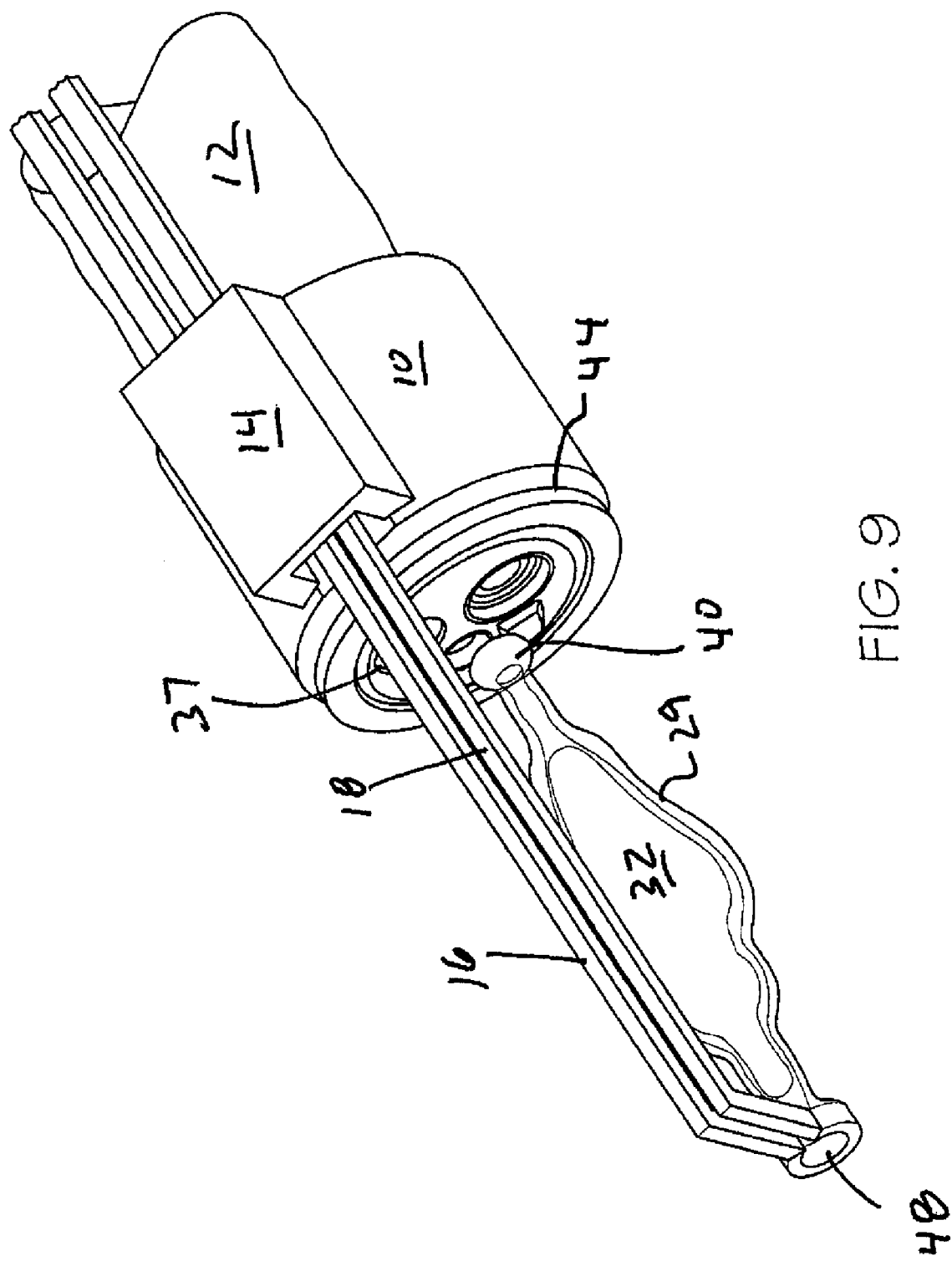
FIG. 9 is a schematic perspective view of the pathway structure and pouch mechanism of FIG. 8 after a vacuum has been applied to the interior of the pouch and the proximal end of the pouch has been released from the pathway structure.

As noted above in connection with the description of FIGS. 5 and 6, the proximal end 26 of the pouch 29 is removably held against the structural pathway 12 (either directly or indirectly against the outer cap 10) by an elastometric member 40. When the specimen 32 is appropriately sized (either the original size or a reduced size from the application of work and the removal of liquid components), the pouch of the exemplary mechanism illustrated in FIGS. 5-9 can be removed from the structural pathway by applying tension (typically from a location external to the patient) to the actuation wires 42. Pulling on the actuation wires 42 applies a corresponding force on the beads 46, which beads 46 pull the proximal end 26 of the pouch off of the structural pathway 12. The elastomeric member 40 is then radially contracted (by virtue of its inherent material properties), which sealingly closes the proximal end 26 of the pouch 29. The pouch 29 is then tethered to the structural pathway from the distal end of the actuator members 16 and 18, as illustrated in FIG. 9. Removing the pouch 29 from the structural pathway 12 in this way, of course, facilitates access to the area of where the recision was made with tools extending through the working channels 37 of the structural pathway 12 while simultaneously keeping the specimen 32 sealingly contained in the pouch.

Figure 10:
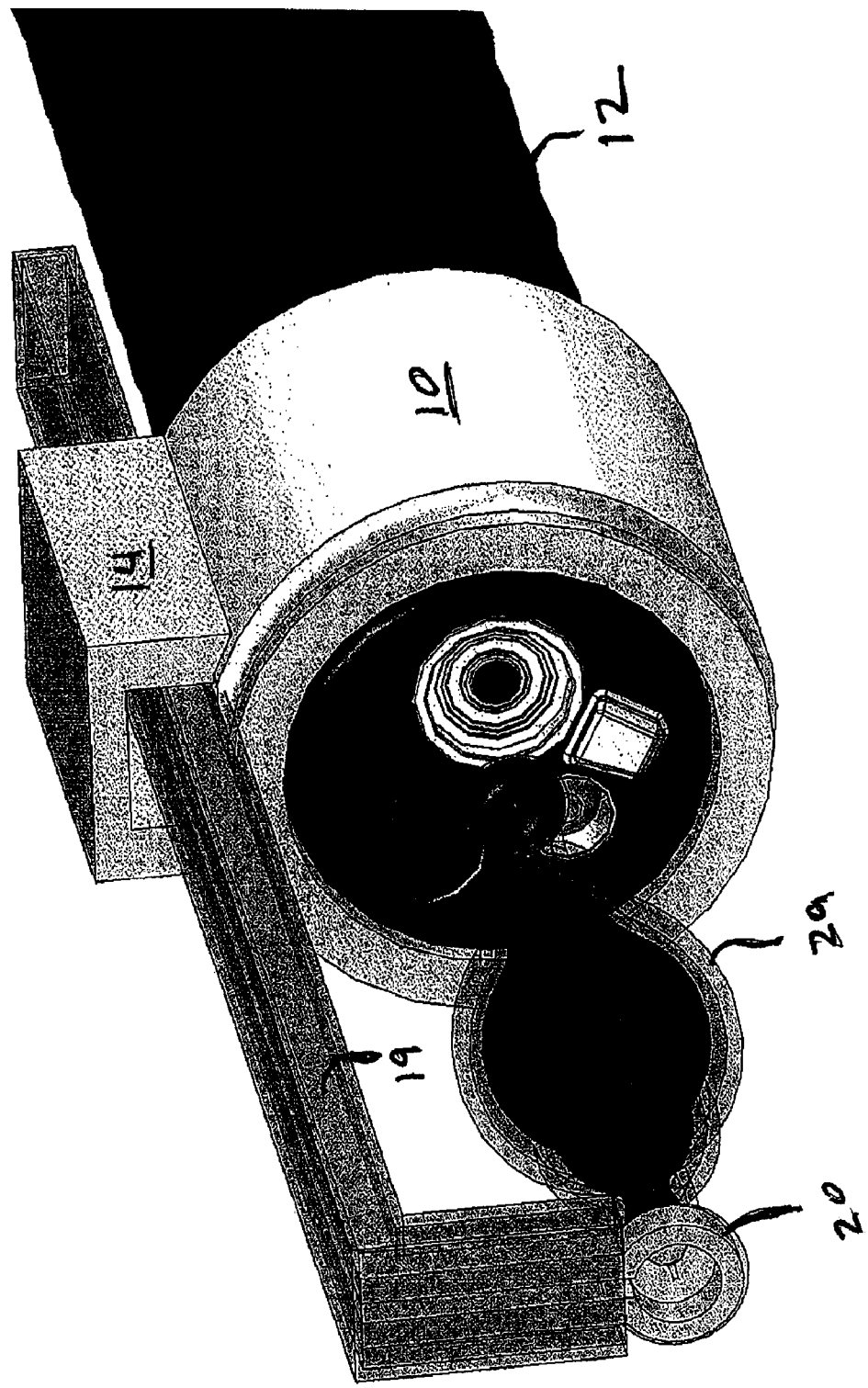
FIG. 10 is a schematic perspective view similar to the view of FIG. 9, but showing actuator components contained within a sheath.

Those skilled in the art appreciate that the actuator components 16 and 18 specifically disclosed in the foregoing exemplary embodiments are elongated flexible cordlike members. If these type of actuator components are utilized, it may be desirable to slidably dispose the actuator components in an outer sheath 19, as illustrated in FIG. 10. The outer sheath 19 used in the exemplary embodiment of FIG. 10, while flexible and bendable, provides sufficient structural rigidity to prevent "buckling" of the actuator components 16 and 18 following the application of a "pushing" force. This, of course, permits cordlike actuator components 16 and 18 to effectuate longitudinal translation of the support member 20 through the application of a "pushing" force against the actuator components 16 and 18 by surgical personal located external to the patient. Similarly, the sheath 19 controls the relative spacing of the actuator components 16 and 18 as those components 16 and 18 are retracted into the sheath 19, thereby effectuating closing of the loop formed by the support member 20 upon retraction of the actuator components 16 and 18.

Those skilled in the art will further appreciate that the invention has applications throughout a wide range of surgical procedures. The method and apparatus can be used, for example for either transluminal or intraluminal procedures. For example, the exemplary embodiment illustrated could be used for removing a polyp from the colon, without piercing the colon wall. Alternatively, the exemplary embodiment illustrated could be used in transluminal procedures in which the surgical site is accessed by piercing the wall of organ, such as the stomach or colon. It also will be appreciated from the exemplary form of the invention illustrated that numerous advantages flow from various aspects the invention. For example, the exemplary form of the invention illustrated eliminates the need to introduce a separate instrument to remove the specimen. This exemplary embodiment also provides a contamination barrier between the resected specimen and surrounding tissue. Finally, in one form of the invention, the volume of the resected specimen is dimensionally altered, and liquid removed, so that the reduced specimen can be removed from the surgical site through a working channel of an endoscopic or laparoscopic instrument used to perform the resection.

The foregoing description of the preferred embodiments of the present invention has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and-are not intended to limit the ordinary meaning of the claims in their fair and broad interpretation in any way.

What is claimed is:

1. A pouch for capturing tissue resected during a surgical procedure, comprising:
   a) a flexible barrier pouch, the barrier pouch having first and second ends with a continuous barrier surface extending between the first and second ends, the barrier pouch being configured to define an internal lumen extending between the first and second ends, the first end of the barrier pouch being adapted for securement about the outside of a structural pathway for defining a repeatable surgical pathway to an internal portion of the body in a position that permits communication between the internal lumen of the barrier pouch and an interior passage of a structural pathway; and
   b) a movable support structure secured to the outside of the structural pathway, the second end of the barrier pouch being connected to the movable support structure, the movable support structure being operative to form an interior lumen in the barrier pouch that is in fluid communication with the pathway structure by longitudinally separating the first and second ends of the barrier pouch as the movable support structure is moved from a first retracted position to a second deployed position, and being further operative to move the second end of the barrier pouch from a first open position creating an opening to the environment external to the barrier pouch to a second closed and sealed position in which the internal lumen of the barrier pouch is sealed and isolated from the environment external to the pouch;
further including a retainer for selectively and releasably securing the first end of the barrier pouch about the external end surface of a pathway structure.

2. A pouch as recited in claim 1 wherein the structural pathway is an endoscope.

3. A pouch as recited in claim 1 wherein the structural pathway is a trocar.

4. A pouch as recited in claim 1 wherein the internal lumen of the barrier pouch is in fluid communication with a vacuum source.

5. A pouch for capturing tissue resected during a surgical procedure, comprising:
   a) a flexible barrier pouch, the barrier pouch having first and second ends with a continuous barrier surface extending between the first and second ends, the barrier pouch being configured to define an internal lumen extending between the first and second ends, the first end of the barrier pouch being adapted for securement about the outside of a structural pathway for defining a repeatable surgical pathway to an internal portion of the body in a position that permits communication between the internal lumen of the barrier pouch and an interior passage of a structural pathway; and
   b) a movable support structure secured to the outside of the structural pathway, the second end of the barrier pouch being connected to the movable support structure, the movable support structure being operative to form an interior lumen in the barrier pouch that is in fluid communication with the pathway structure by longitudinally separating the first and second ends of the barrier pouch as the movable support structure is moved from a first retracted position to a second deployed position, and being further operative to move the second end of the barrier pouch from a first open position creating an opening to the environment external to the barrier pouch to a second closed and sealed position in which the internal lumen of the barrier pouch is sealed and isolated from the environment external to the pouch;
further including a clip adapted for circumferential disposition on the end of the structural pathway, wherein the first end of the barrier pouch is secured to the clip.

6. A pouch as recited in claim 5 wherein the structural pathway is an endoscope.

7. A pouch as recited in claim 5 wherein the structural pathway is a trocar.

8. A pouch as recited in claim 5 wherein the internal lumen of the barrier pouch is in fluid communication with a vacuum source.

9. In combination with a structural pathway for defining a repeatable surgical pathway to an internal portion of a body, the structural pathway having a proximal end for location externally of a patient and a distal end for insertion into a lumen of a patient, a flexible barrier mechanism for isolating and removing surgically resected tissue, the flexible barrier mechanism comprising:
   a) a pouch formed of a longitudinally expandable continuous barrier membrane with first and second ends and an internal lumen defined by the membrane extending between the first and second ends, the first end of the pouch being secured in sealed relationship about the external peripheral surface of the distal end of the structural pathway;
   b) a movable support structure located outside of the structural pathway for longitudinally separating the first and second ends of the pouch relative to each other to selectively form an interior lumen in the barrier pouch and move the second end of the membrane between an open position in which the internal lumen is open to the ambient environment for receiving a surgically resected specimen at a surgical site and a second closed position in which the internal lumen is sealed from the ambient environment; and
   c) an actuator located outside of the structural pathway for selectively moving the second end of the membrane between the open and sealed positions;
wherein the first end of the pouch is connected to a clip disposed on the outer periphery of the distal end of the structural pathway.

10. A structure as recited in claim 9 wherein the movable support structure moves the second end of the pouch longitudinally from a first retracted position to a second deployed position.

11. A structure as recited in claim 9 wherein the internal lumen of the pouch is in fluid communication with a vacuum source.

12. A structure as recited in claim 9 further including a removable retainer for selectively and releasably securing the first end of the pouch about the external surface of the structural pathway.

* * * * *